United States Patent [19]

Ahlers et al.

[11] Patent Number: 5,428,112
[45] Date of Patent: Jun. 27, 1995

[54] CROSSLINKED, NITROGEN-CONTAINING VINYL COPOLYMERS, PROCESSES FOR THEIR PREPARATION AND THE USE OF THESE COMPOUNDS

[75] Inventors: Michael Ahlers, Mainz; Heiner Glombik, Hofheim am Taunus; Stefan Müllner, Hochheim; Axel Walch, Frankfurt am Main, all of Germany

[73] Assignee: Hoechst Aktiengesellschaft, Germany

[21] Appl. No.: 95,624

[22] Filed: Jul. 21, 1993

[30] Foreign Application Priority Data

Jul. 22, 1992 [DE] Germany ............ 42 24 110.3

[51] Int. Cl.⁶ .............................................. C08F 8/12
[52] U.S. Cl. .................. 525/326.7; 525/328.2; 525/328.3; 525/328.4; 525/355
[58] Field of Search ............. 525/328.2, 328.3, 326.7

[56] References Cited

U.S. PATENT DOCUMENTS

| | | |
|---|---|---|
| 3,558,581 | 1/1971 | Beermann . |
| 4,238,579 | 12/1980 | Leonard . |
| 4,421,602 | 12/1983 | Brunnmueller et al. . |
| 4,444,667 | 4/1984 | Burkert et al. . |
| 4,774,285 | 9/1988 | Pfohl et al. . |
| 4,880,497 | 11/1989 | Pfhol et al. . |
| 4,978,427 | 12/1990 | Pfohl et al. . |

FOREIGN PATENT DOCUMENTS

| | | |
|---|---|---|
| 01622388 | 11/1985 | European Pat. Off. . |
| 02199910 | 4/1987 | European Pat. Off. . |
| 0339371 | 11/1989 | European Pat. Off. . |
| 0379161 | 7/1990 | European Pat. Off. . |

OTHER PUBLICATIONS

Derwent 91-274735/38 which relates to DE A-40-07-312.
Patent Abstracts of Japan, vol. 10, No. 208 (C-361)(2264), Jul. 22, 1986.
Dissertation of Thomas Fisher, Marburg, Apr. 1992.

*Primary Examiner*—Bernard Lipman
*Attorney, Agent, or Firm*—Barbara V. Maurer

[57] ABSTRACT

Crosslinked, nitrogen-containing vinyl copolymers having units of the formula I

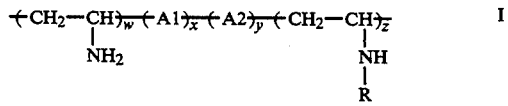

and physiologically tolerated salts thereof, in which, in formula I, A1, A2, R, w, x, y and z have the meanings given, a process for their preparation and the use of the compounds as medicaments, active compound carriers and foodstuff auxiliaries are described.

2 Claims, No Drawings

CROSSLINKED, NITROGEN-CONTAINING VINYL COPOLYMERS, PROCESSES FOR THEIR PREPARATION AND THE USE OF THESE COMPOUNDS

DESCRIPTION

The invention relates to crosslinked, nitrogen-containing vinyl copolymers and a process for their preparation. On the basis of their ability to adsorb bile acids, they are suitable as medicaments in particular for reducing the blood cholesterol level. They are furthermore suitable for use as an active compound carrier, as a foodstuff auxiliary and as a foodstuff additive. The invention therefore also relates to the use of the compounds and to a process for their preparation.

Bile acids have an important physiological function in fat digestion. As end products of cholesterol metabolism they are synthesized in the liver, stored in the gallbladder and released into the intestine, where they display their physiological action. The major proportion of bile acids secreted is recovered via the enterohepatic circulation (about 20–25 g/day). Suppression of this resorption reduces the bile acid pool in the liver and thus causes an increased absorption of cholesterol from the blood circulation, as well as stimulation of endogenous cholesterol synthesis. For this, the number of hepatic LDL receptors on the membranes of the liver cells increases, so that catabolism of the cholesterol-containing LDL particles is accelerated and the cholesterol content in the blood is reduced.

It is known that bile acids can be bonded to insoluble, basic, crosslinked polymers, such as polyethyleneimines (cf., for example, EP-A-0379 161) or polyvinylimidazoles (cf. EP-B-0162 388), and are therefore regarded as being inhibition of bile acid resorption in the intestine, especially in the small intestine, seems desirable. For example, choleogenic diarrhea following ileum resection or increased blood cholesterol levels are treated in this manner.

A very high daily dose in particular is to be maintained for the ion exchanger resins used as lipid-lowering agents, such as colestipol and colestryamine. It is, for example, 12–24 g for colestryamine, and 32 g in the highest instance, and 15–30 g for colestipol.

This high dosage and the unpleasant smell, taste and consistency make patient compliance difficult.

Side effects of these ion exchange resins are also to be attributed to the lack of selectivity (for example avitaminoses). For both preparations, a therapeutic importance has been described in combination with other hypolipidemic drugs, such as fibrate, HMG-CoA reductase inhibitors and probucol (cf., for example, M. N. Cayen, Pharmac. Ther. 29, 187 (1985) and 8th International Symposium on Atherosclerosis, Rome, Oct. 9–13, 1988, Abstracts pages 544,608,710), the effects achieved also allowing therapy of severe cases of hyperlipidemia. It therefore seems important to discover substances which are suitable for the action principle described without having the disadvantages of the preparations currently used.

The following features of the preparations mentioned and in particular of colestipol are to be regarded as worthy of improvement:

1. The high daily doses, which are to be attributed to a low bonding rate in isotonic solution and to partial re-release of the bile acid adsorbed.
2. The qualitative shift in the bile acid composition of the bile with a decreasing tendency for chenodeoxycholic acid and the associated increasing risk of cholelithiasis.
3. The absence of a suppressing action on the cholesterol metabolism of the intestinal bacteria.
4. The excessively high bonding rate of vitamins and drugs, which may necessitate a substitution requirement for these substances and blood level checks.
5. Inadequate purity and stability of the polymers (the risk of splitting off of amino and ammonium groups from colestyramine).
6. Inadequate patient compliance because of a) the "sandy" consistency (colestyramine=hard gel polymer) and b) the unpleasant smell and taste.

Variations to the preparations used to date, such as, for example, introduction of spacers between ammonium groups and the polymer main chain in the case of colestyramine (EP-A-0 404 062), do not lead to a decisive reduction in the disadvantages described.

The object of the present invention was to provide compounds having novel polymer structures which bond bile acids to a high degree, depending on the concentration. These compounds moreover should not have the existing disadvantages of the exchanger resins used to date, or should no longer have these disadvantages to the known extent.

The object is achieved and the deficiencies described are overcome with the insoluble, water-binding, nitrogen-containing vinyl copolymers of the formula I.

The invention therefore relates to crosslinked, nitrogen-containing vinyl copolymers having units of the formula I

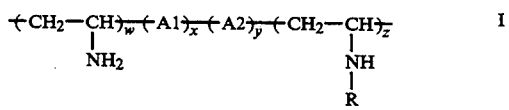

and physiologically tolerated salts thereof, in which, in formula I, w is 0.1–0.98,
x is 0.0–0.8,
y is 0.0–0.3 and
z is 0.0–0.6, in which $w+x+y+z$ is 1, $x=0$ only if $y\neq 0$, $y=0$ only if at the same time $x\neq 0$ and $z\neq 0$ and $R=R^4$, and in which

A1

1. is a hydrolysis-stable radical of the formula

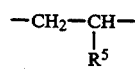

in which $R^5$ is a linear or branched alkoxy radical having 3 to 18 carbon atoms, a cycloalkyl radical having 5 to 8 carbon atoms or a phenoxy, tolyl, 4-(tert-butyl)-phenyl, 4-aminophenyl, N-carbazyl, N-imidazolyl, 2-pyridinyl or 4-pyridinyl radical, or 2. is a hydrolysis-stable radical of the formula

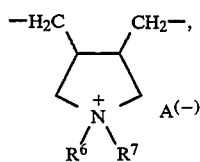

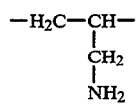

or

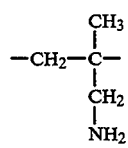

in which $R^6$ is an alkyl radical having 1 to 18 carbon atoms and $R^7$ is H or, if $R^6$ is alkyl having 1 to 6 carbon atoms, an alkyl radical having 1 to 6 carbon atoms,

A2

1. is the radical of a hydrolysis-stable crosslinking agent of the formula

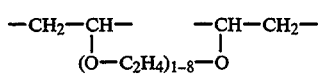

or 2. is a radical of the formula

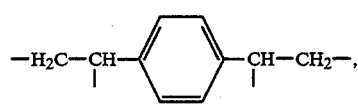

or

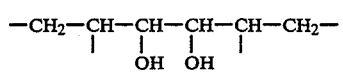

and in which

R is $R^1$—X, $R^2$—X, $R^3$ $R^4$, in which $R^1$ is a substituent selected from the group comprising:

1. —(CH$_2$)$_n$—CH$_3$, in which n is an integer from 3 to 21, branched alkyl having 3 to 21 carbon atoms or straight-chain or branched alkenyl having up to 21 carbon atoms,
2. cycloalkyl, cycloalkenyl having in each case 5–12 carbon atoms or mono-, di- or trisubstituted cycloalkyl or cycloalkenyl having in each case 5–12 ring carbon atoms and
3. aryl, arylalkyl or arylalkenyl, in which the aryl radicals are mono- or polynuclear, can be mono- to trisubstituted and can contain hetero atoms and X is a single bond or a bridge group or a spacer, and $R^2$ is a hydrophilic or amphiphilic substituent selected from the group comprising:

1. 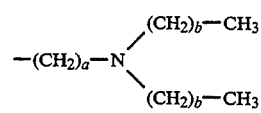

2. 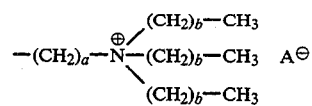

3. 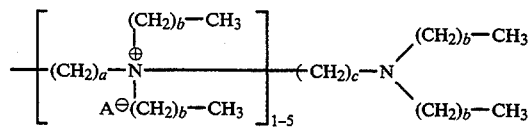

4. —(CH$_2$)$_c$—B, in which B is a pyrrolidinyl, piperidinyl or morpholinyl radical bonded via N,
5. —(CH$_2$)$_a$-D$^\oplus$A$^\ominus$, in which D$^\oplus$ is pyridinium, pyrimidinium or imidazolinium and 6. 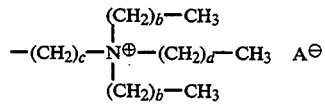

in which, in the substituents mentioned under 1. to 6., a is an integer from 2 to 16,
b is zero, 1, 2 or 3,
c is an integer from 2 to 6,
d is an integer from 6 to 17 and
A is a physiologically tolerated anion, $R^3$ is a radical selected from the group comprising
1. a cholic acid which is bonded via the 3-α-OH or 24-COOH function directly or via a spacer,
2. a tauro- or glycocholic acid which is bonded via the 3α-OH or tauro or glyco function directly or via a spacer and
3. a hydrophilic cyclic radical or a glucopyranuronic acid radical and $R^4$ represents a crosslinking radical selected from the group comprising:
1. W—(CH$_2$)$_e$—W and
2. W—(CH$_2$—CH$_2$O)$_f$—CH$_2$—CH$_2$—W in which W is a single bond,

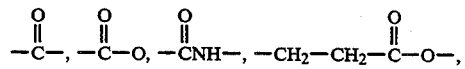

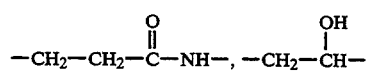

and in which
e is an integer from 3 to 12 and
f is an integer from 1 to 6.

In the statements above and below:

aryl is a mono- or polynuclear aromatic hydrocarbon radical having 6 to 14 carbon atoms, in which, in the case of polynuclear radicals, the aryl groups are fused with one another or bonded to one another via C—C bonds or via bridge members such as —O—, —COO— or —CONH—. The term aryl furthermore also includes 5- to 14-membered heteroaryl having 1 hetero atom or 2 non-adjacent, identical or different hetero atoms selected from the group comprising oxygen and nitrogen.

Aryl is, in particular, phenyl, arylalkyl is benzyl or phenylethyl and arylalkenyl is

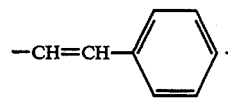

Examples of aromatic radicals having 1 or 2 hetero atoms are radicals of quinolinecarboxylic, benzimidazolecarboxylic, furancarboxylic, nicotinic and cumarilic acid.

The cycloalkyl and cycloalkenyl radicals are optionally mono-, di- or trisubstituted by hydroxyl, ($C_1$–$C_6$)-alkyl and/or ($C_1$–$C_6$)-alkoxy radicals, the substituents being identical or different in the case of polysubstitution. Corresponding statements also apply to the substituents on the aryl: a possible radical is, for example, a triethylbenzoic acid radical.

The bridge member X is

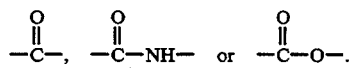

The spacer X has the formula

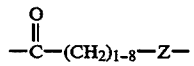

where Z is

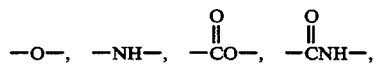

and, in the case of 3–8 methylene groups, a central $CH_2$ group can be replaced by oxygen.

$R^1$—X is, for example, a radical of the formula

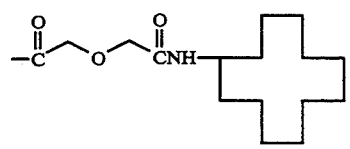

An example of R in the meaning mentioned under $R^3$ 1. is the radical of the formula

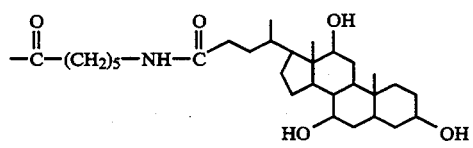

A hydrophilic cyclic radical R according to $R^3$ 3. is a cyclodextrin radical or a functionalized 7- to 18-membered carbon-containing azamacrocyclic radical having 2 to 4 nitrogen atoms and optionally 2, 3 or 4 oxygen atoms, which are separated via ethylene groups, such as, for example, 1,4,7-triazacyclononane, a cyclene or cyclam radical or 1,4-diaza-18 crown 6.

The radical $R^1$ is preferably hydrophobic.

If b occurs more than once in a structure, then b is identical or different, c is always identical in a structure and W is always identical.

The vinyl copolymers according to the invention having units of the formula I are branched and crosslinked. As is customary in polymeric chemistry, the groups shown in formula I are distributed randomly over the entire polymer or arranged in accordance with their copolymerization parameters.

The invention furthermore relates to a process for the preparation of vinyl copolymers having units of the formula I, which comprises preparing a compound of the formula II

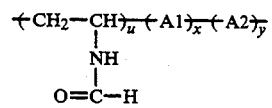

in which A1, A2, x and y have the meanings given in the case of formula I and u is 0.1–0.98, from vinylformamide by copolymerization, hydrolyzing this product to give a compound of the formula III

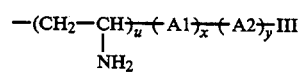

in which A1, A2, x and y have the meanings given in the case of formula I and u has the meaning given in the case of formula II, and then optionally forming derivatives by customary methods, to give a compound having units of the formula I or physiologically tolerated salts thereof.

The crosslinked, nitrogen-containing copolymers are prepared by crosslinking copolymerization with the monomer content $A_2$ or by polymer-analogous crosslinking (content of $R^4$) using crosslinking agents from the group comprising dialkyl agents, such as $\alpha,\omega$-dibromoalkanes, ditosylates and diisocyanates, or from the group comprising diacids, diacrylates and diacrylamides, or diepoxides.

In formula II, u is the sum of w and z. In the compounds according to the invention, z contents are present as the derivative (R) and w contents are present as free vinylamine units or as physiologically tolerated salts thereof. The derivatization of the vinylamine contents u is preferably carried out such that z is less than 0.6 times w.

Vinyl copolymers in which R is $R^1$—X, or and in $R^2$—X $R^3$ and in which at the same time z is 0.1 to 0.3 are preferred. If R is $R^4$, z is preferably 0.0 to 0.1.

In the preparation of the copolymers, the content of groups A1 is 0 to 80%, preferably 0 to 50%, in particular 10 to 30%. The content of groups A2 is 0 to 30%, preferably 2 to 20%, in particular 5–15%.

The following equation illustrates the process by an example of crosslinking copolymerization, for example with y times triethylene glycol divinyl ether

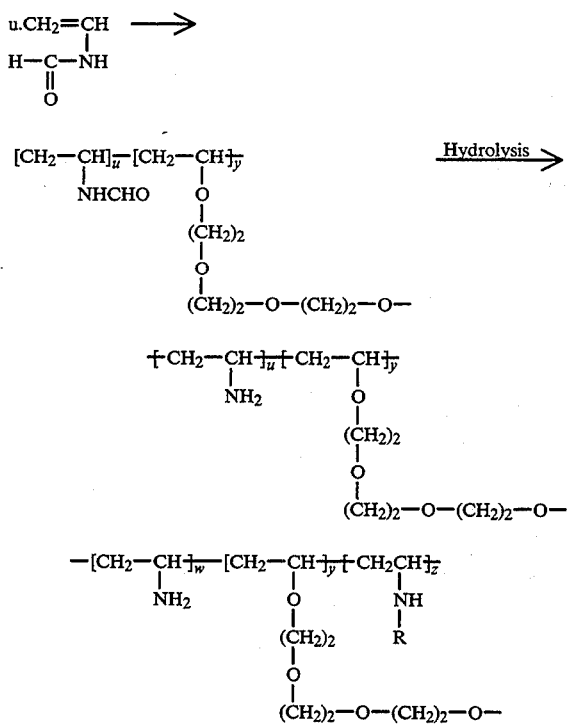

On the basis of their properties, the copolymers having units of the formula I can be used as medicaments, for example as lipid-reducing agents, as satiation promoters, or as a foodstuff additive and foodstuff auxiliary. The invention therefore also relates to these uses and medicaments based on compounds having units of the formula I.

By using the compounds according to the invention, the customary dosage of the bile acid adsorbers used to date for treatment of hypercholesterolemia can be reduced considerably. The problem of dosage and compliance therefore no longer results. In addition, compliance is also improved by the fact that the compounds have a soft gel character and a neutral taste and smell, so that no flavor and smell compensators are needed.

The effectiveness of the active compounds described can be increased by special microformulations. For this, the compounds are converted into swellable microparticles by means of various techniques (for example mechanical micronization). Microparticles can also be obtained during the synthesis by the process procedure, such as latex polymerization. The swellable microparticles are distinguished by the fact that the active compound is distributed over a very large adsorptive surface area, so that the bile acid bonding sites are readily accessible.

Film-coated tablets which have the same activity in vitro as the compounds in powder form can be prepared from the compounds as a presentation form. They comprise, for example, only 40 mg of pharmaceutically customary auxiliary per 250 mg of active compound.

The reduction in serum cholesterol level to be achieved with the compounds can be improved further by simultaneous use of other non-systemically or systemically acting lipid-reducing agents (for example HMG-CoA reductase inhibitors) in the context of a combination therapy.

Since the compounds interrupt the enterohepatic circulation, they are also suitable for use in cases of oral toxification.

The compounds moreover can be employed as satiation promoters because of their water uptake capacity.

Since the compounds according to the invention are readily swellable and bond acids, they can be employed as antacids for the treatment of excessive gastric acid production and are thus used as agents against gastritis and *Ulcus ventriculi* or *duodeni.*

Because of their interaction with cholesterol, the compounds are capable of adsorbing cholesterol consumed with food. The content of cholesterol in the food is therefore bonded and is not absorbed by the body.

The compounds according to the invention furthermore are also suitable as foodstuff auxiliaries. Thus, for example, cholesterol is adsorbed from milk or egg constituents. The resulting foodstuffs are distinguished by a reduced cholesterol content.

Compounds having units of the formula I are suitable as mucoadhesive transportation systems for active compounds. They form highly hydrateable polymer matrices which have groups which form hydrogen bridges and cationic groups and a high flexibility of the polymer chain, and can additionally be substituted by hydrophobic units. The compounds are therefore capable of prolonging the residence time of a bonded or adsorbed active compound in the stomach or small intestine. They are adsorbed as active compound carriers onto the mucosal layer of the gastrointestinal wall, the positively charged groups of the copolymers interacting with the negatively charged groups of the terminal sialic acids of the mucin molecules in order thus to cause delayed transportation of the active compounds through the gastrointestinal tract. At the same time, the absorption of the active compound is improved by the nature of the interaction.

In vitro Tests

The compounds are tested for their bile acid bonding capacity in an in vitro test.

10 mg of polymer sample are dissolved in 18 ml of buffer (PBS, pH 7.4, 15 mM or 37 mM), the solution is stirred at room temperature for 1 hour, 2 ml of Na taurocholate (37 mM) are added and the mixture is incubated at room temperature for 2 hours. The solid polymer-taurocholate complexes are separated off by filtration. The content of non-bonded taurocholate is determined by means of HPLC (column: RP-8 LiChrosorb; eluent: methanol/citrate buffer pH 4 (Riedel de Haen)/water 6:1:1).

At a mixing ratio of polymer sample to sodium taurocholate of 1/4 (w/w), the following taurocholate adsorption values result, as the molar ratio:

Compound Example 1): 17 mol %
Compound Example 2): 25 mol %
Compound Example 3): 24 mol %
Compound Example 5): 26 mol %
Compound Example 6): 29 mol %
Compound Example 7): 25 mol %

EXAMPLES

Example 1

120 g of vinylformamide and 52 g of triethylene glycol divinyl ether are dissolved in toluene with 1.4 g of 4,4'-azocyanopentanoic acid, and the solution is flushed with $N_2$. It is stirred at 60° C. for 30 minutes and at 70°

C. for 6 hours. The polymer which has precipitated is filtered off with suction, washed with toluene and dried.

Yield: 161 g 152 g of the copolymer are suspended in 2.5 l of half-concentrated HCl and the suspension is stirred at 80° C. for 2 hours. After addition of 0.5 l of concentrated HCl, the mixture is stirred at 80° C. for a further 6 hours. The product is filtered off with suction and, to adjust the hydrochloride content, is resuspended in H$_2$O and titrated to pH=4. It is precipitated again in acetone and extracted several times by stirring with acetone, before being dried in vacuo at 50° C.

Yield: 117 g

Example 2

60 g of vinylformamide, 8.6 g of triethylene glycol divinyl ether and 0.6 g of ACPA are polymerized in 350 ml of toluene as described under 1) and the product is then hydrolyzed. To adjust the hydrochloride content, it is resuspended in ethanol/H$_2$O 1:1.

Example 3

3 g of compound from Example 1 are dispersed in 200 ml of H$_2$O at pH 10, 0.55 g of dimethyl-chloroethylamine hydrochloride is added and the mixture is stirred at the same pH at 80° C. for 8 hours. The polymer is precipitated in acetone and taken up in H$_2$O/ethanol, the mixture is titrated to pH=4 and the product is precipitated again in acetone and extracted by stirring. Drying is carried out at 50° C. in vacuo.

Example 4

5 g of vinylformamide, 1.3 g of vinylimidazole, 1.4 g of triethylene glycol divinyl ether and 0.07 g of azocyanopentanoic acid are introduced into 40 ml of water. The solution is flushed with N$_2$ and stirred at 60° C. for 6 hours. After addition of 40 ml of H$_2$O and 60 ml of half-concentrated HCl, the mixture is stirred at 70° C. for 3 hours, and after addition of 90 ml of concentrated HCl, it is stirred at 70° C. for a further 4 hours. Acetone is added to the batch, the product is filtered off with suction and suspended in H$_2$O and the pH is brought to 4 with NaOH. The product is precipitated again in acetone and extracted several times by stirring with acetone, before being dried in vacuo at 50° C.

Example 5

5.7 g of vinylformamide, 1.9 g of N-vinylimidazole and 0.1 g of azocyanopentenoic acid are introduced into 47 ml of H$_2$O and the mixture is flushed with N$_2$ and stirred at 70° C. for 7 hours. The copolymer formed is precipitated in acetone, dissolved in H$_2$O for hydrolysis, and stirred with 2 mol of NaOH per mol of formamide content at 70° C. for 6 hours. The batch is brought to pH 6 with HCl and diluted with 1 part of methanol and the product is precipitated in acetone.

Degree of substitution according to NMR: 20%.
Yield: 5.0 g 2 g of the copolymer are brought to pH 10 in 15 ml of H$_2$O with NaOH, 0.36 g of dibromohexane (5 mol %) and 120 mg of NaOH are added and the mixture is stirred at 90° C. for 6 hours. After half an hour, gel formation starts.

The pH is brought to 1 with 1N HCl and the product is precipitated inversely by addition of acetone. Two further precipitations in acetone are carried out at pH 5.

Yield: 2.1 g

Example 6

Analogously to Example 5, 5 g of vinylformamide and 2.8 g of N-vinylimidazole are polymerized with 0.11 g of azocyanopentanoic acid in 50 ml of H$_2$O at 70° C. for 7 hours. Basic hydrolysis is then carried out.

Degree of substitution according to NMR: 32%
Yield: 4.4 g.

1.5 g of the copolymer are crosslinked with 0.26 g of dibromohexane and 84 mg of NaOH in 15 ml of H$_2$O. Working up is carried out analogously to Example 5.

Yield: 1.2 g.

Example 7

3.6 g of vinylformamide and 4.7 g of N-vinylimidazole are polymerized with 0.12 g of azocyanopentanoic acid in 52 ml of H$_2$O at 70° C. for 7 hours analogously to Example 5. Basic hydrolysis is carried out with 1.4 g of NaOH.

Degree of substitution according to NMR: 53%.
Yield: 4.8 g.

1.5 g of the copolymer are crosslinked with 0.24 g of dibromohexane and 77 mg of NaOH in 15 ml of H$_2$O. Working up is carried out analogously to Example 5.

Yield: 0.9 g.

We claim:

1. A crosslinked nitrogen-containing vinyl copolymer having units of the formula I

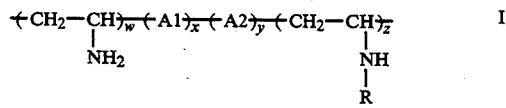

or a physiologically tolerated salt thereof, in which, in formula I, w is 0.1–0.98,
x is 0.0–0.8,
y is 0.0–0.3 and
z is 0.0–0.6, in which w+x+y+z is 1, x=0 only if y≠0, y=0 only if at the same time x≠0 and z≠0 and R=R$^4$, and in which

A1

1. is a hydrolysis-stable radical of the formula

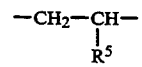

in which R$^5$ is a linear or branched alkoxy radical having 3 to 18 carbon atoms, a cycloalkyl radical having 5 to 8 carbon atoms or a phenoxy, tolyl, 4-(tert-butyl)phenyl, 4-aminophenyl, N-carbazyl, N-imidazolyl, 2-pyridinyl or 4-pyridinyl radical, or 2. is a hydrolysis-stable radical of the formula

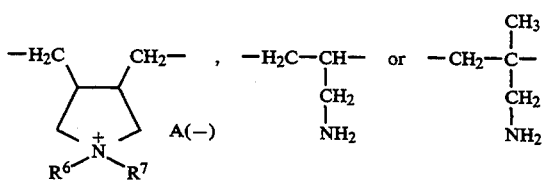

in which R$^6$ is an alkyl radical having 1 to 18 carbon atoms and R$^7$ is H or, if R$^6$ is alkyl having 1 to 6 carbon atoms, an alkyl radical having 1 to 6 carbon atoms, A2
1. is the radical of a hydrolysis-stable crosslinking agent of the formula

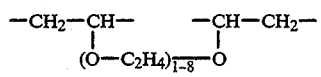

or 2. is a radical of the formula

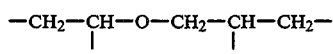

or

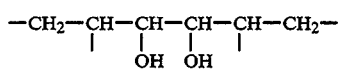

and in which
R is $R^1$—X, $R^2$—X, $R^3$ or $R^4$, in which
$R^1$ is a substituent selected from the group consisting of:
1. —$(CH_2)_n$—$CH_3$, in which n is an integer from 3 to 21, branched alkyl having 3 to 21 carbon atoms or straight-chain or branched alkenyl having up to 21 carbon atoms,
2. cycloalkyl, cycloalkenyl having in each case 5–12 carbon atoms or mono-, di- or trisubstituted cycloalkyl or cycloalkenyl having in each case 5–12 ring carbon atoms and
3. aryl, arylalkyl or arylalkenyl, in which the aryl radicals are mono- or polynuclear, can be mono- to trisubstituted and can contain hetero atoms and X is a single bond or a bridge group or a spacer, and
$R^2$ is a hydrophilic or amphiphilic substituent selected from the group consisting of:

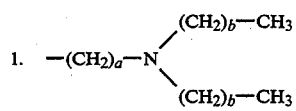

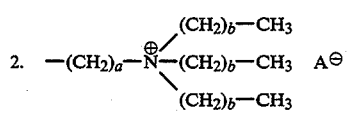

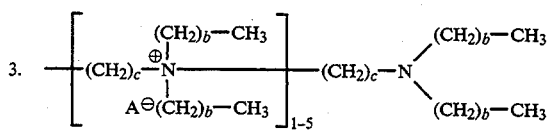

4. —$(CH_2)_c$—B, in which B is a pyrrolidinyl, piperidinyl or morpholinyl radical bonded via N,
5. —$(CH_2)_a$-$D^{\oplus}A^{\ominus}$, in which $D^{\oplus}$ is pyridinium, pyrimidinium or imidazolinium and

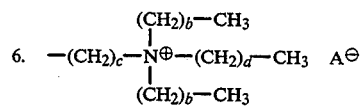

in which, in the substituents mentioned under 1. to 6.,
a is an integer from 2 to 16,
b is zero, 1, 2 or 3,
c is an integer from 2 to 6,
d is an integer from 6 to 17 and
A is a physiologically tolerated anion,
$R^3$ is a radical selected from the group consisting of
1. a cholic acid which is bonded via the 3-α-OH or 24-COOH function directly or via a spacer,
2. a tauro- or glycocholic acid which is bonded via the 3α-OH or tauro or glyco function directly or via a spacer and
3. a hydrophilic cyclic radical or a glucopyranuronic acid radical and
$R^4$ represents a crosslinking radical selected from the group consisting of:
1. W—$(CH_2)_e$—W and
2. W—$(CH_2$—$CH_2O)_f$—$CH_2$—$CH_2$—W
in which W is a single bond,

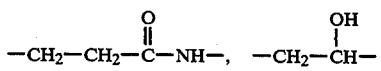

and in which
e is an integer from 3 to 12 and
f is an integer from 1 to 6.
2. A pharmaceutical preparation comprising a copolymer as claimed in claim 1.

* * * * *